US009176101B2

(12) United States Patent
Moeller

(10) Patent No.: US 9,176,101 B2
(45) Date of Patent: Nov. 3, 2015

(54) ROTARY SHEAR INJECTOR VALVE WITH DISPLACED ROTOR GROOVES

(75) Inventor: Mark W. Moeller, Kingston, MA (US)

(73) Assignee: Waters Technologies Corporation, Milford, MA (US)

(*) Notice: Subject to any disclaimer, the term of this patent is extended or adjusted under 35 U.S.C. 154(b) by 280 days.

(21) Appl. No.: 13/638,984

(22) PCT Filed: Apr. 6, 2011

(86) PCT No.: PCT/US2011/031345
§ 371 (c)(1),
(2), (4) Date: Dec. 10, 2012

(87) PCT Pub. No.: WO2011/130071
PCT Pub. Date: Oct. 20, 2011

(65) Prior Publication Data
US 2013/0276520 A1 Oct. 24, 2013

(51) Int. Cl.
*G01N 30/02* (2006.01)
*F16K 11/074* (2006.01)
*G01N 30/20* (2006.01)

(52) U.S. Cl.
CPC ............ *G01N 30/02* (2013.01); *F16K 11/0743* (2013.01); *G01N 2030/202* (2013.01)

(58) Field of Classification Search
CPC ..... G01N 30/02; G01N 30/32; G01N 30/461; G01N 30/36; G01N 2030/326; G01N 2030/328; G01N 2030/324; G01N 30/20; G01N 2030/202; F16K 11/0743
USPC ................ 137/625.21; 251/368; 204/192.38; 73/61.52, 61.55, 61.56
See application file for complete search history.

(56) References Cited

U.S. PATENT DOCUMENTS

| 3,199,274 A * | 8/1965 | Norem et al. ................... 96/104 |
| 3,964,513 A * | 6/1976 | Molner ..................... 137/624.18 |
| 4,068,528 A * | 1/1978 | Gundelfinger ............. 73/864.84 |
| 4,243,071 A * | 1/1981 | Shackelford ............. 137/625.46 |
| 4,506,558 A * | 3/1985 | Bakalyar ..................... 73/863.72 |
| 5,207,109 A * | 5/1993 | Olsen ......................... 73/863.73 |
| 7,574,901 B2 * | 8/2009 | Iwata .......................... 73/61.56 |
| 2009/0050212 A1 * | 2/2009 | Dourdeville et al. ........... 137/14 |

* cited by examiner

*Primary Examiner* — Daniel S Larkin
(74) *Attorney, Agent, or Firm* — Waters Technologies Corporation

(57) ABSTRACT

A valve includes a stator that has fluidic ports in a seal surface, and a rotor that has a seal surface contacting the stator's seal surface. The rotor has through-holes that extend from the seal surface to a back surface, providing fluidic communication with a conduit disposed adjacent to the back surface of the rotor. A chromatography apparatus includes a sample source, a solvent source having a higher operating pressure than the sample source, and an injector valve. A method of performing chromatography includes loading a sample with a valve in a load-state configuration that disposes a sample source in fluidic communication with a conduit disposed adjacent to a back surface of the rotor, and injecting the loaded sample with the valve in an inject-state configuration that disposes a solvent source in fluidic communication with a column via at grooves adjacent to a front seal surface of the rotor.

5 Claims, 4 Drawing Sheets

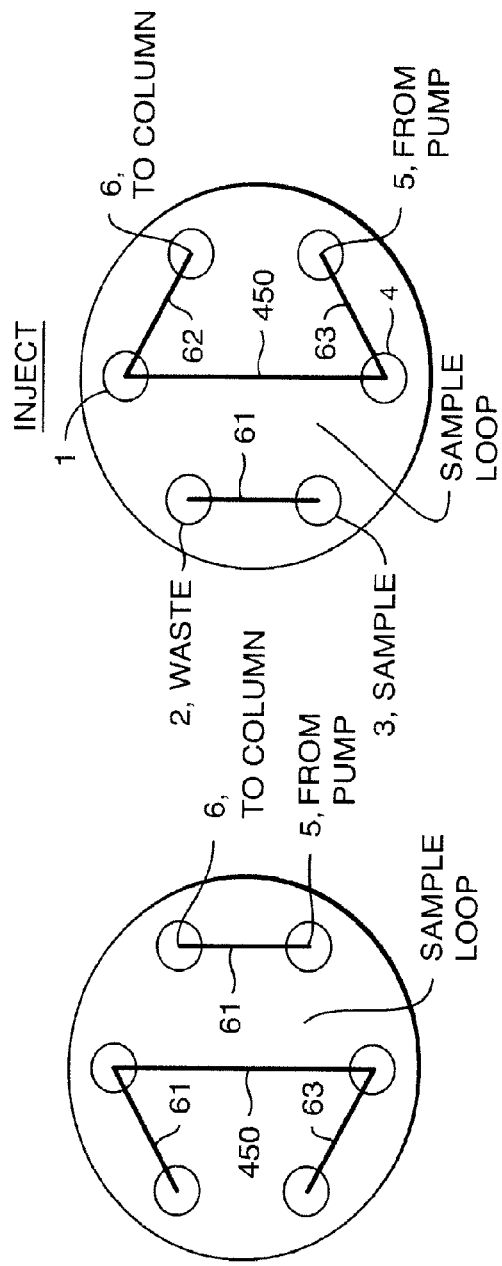
FIG. 4C PRIOR ART
FIG. 4B PRIOR ART
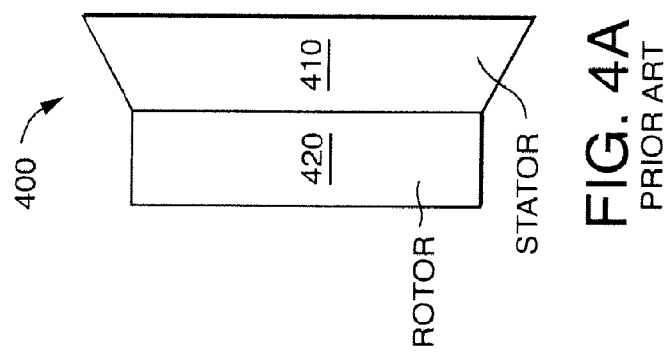
FIG. 4A PRIOR ART

ROTARY SHEAR INJECTOR VALVE WITH DISPLACED ROTOR GROOVES

CROSS-REFERENCE TO RELATED APPLICATIONS

This application claims priority to U.S. Provisional Application No. 61/323,524, filed on Apr. 13, 2010, the entire contents of which are incorporated herein by reference.

TECHNICAL FIELD

The invention generally relates to valves, and, more particularly, to high-pressure valves that have moving parts and are used in chemical-processing apparatus.

BACKGROUND INFORMATION

The invention relates to valves having parts that move under loads. These parts often must retain fluid integrity, that is, such parts should not leak fluids. As a valve is cycled, however, between positions, the loads placed on the moving parts cause wear.

Some valves are subjected to high pressures. For example, sample injector valves, in high performance liquid chromatography (HPLC) apparatus, are exposed to pressures of approximately 1,000 to 5,000 pounds per square inch (psi), as produced by common solvent pumps. Higher pressure chromatography apparatus, such as ultra high performance liquid chromatography (UHPLC) apparatus, have solvent pumps that operate at pressures up to 15,000 psi or greater.

As the pressure of a system increases, wear and distortion of a valve's components, such as a rotor and a stator, tends to increase, and the valve's expected cycle lifetime may be reduced.

SUMMARY OF THE INVENTION

The invention arises, in part, from the realization that a valve—in a chemical-processing apparatus—having sliding components, can advantageously dispose conduits adjacent to both surfaces of a rotor, or adjacent only to the back surface of a rotor. Such configurations can remove grooves from the sliding surfaces of a valve and/or remove a groove that only experiences relatively low pressure from a contact surface that is subjected to high pressures. Thus, for example, the invention is particularly well suited to provide improved rotary shear injector valves for delivery of samples in an HPLC or higher-pressure apparatus.

Accordingly, one embodiment of the invention features a rotary shear chromatography valve. The valve includes a stator and a rotor. The stator defines at least one fluidic port in a seal surface. The rotor has a seal surface contacting the seal surface of the stator. The rotor defines at least one through-hole that extends from the seal surface of the rotor to a back surface of the rotor and provides fluidic communication with a conduit disposed adjacent to the back surface of the rotor.

Another embodiment of the invention features a chromatography apparatus. The apparatus includes a sample source, a solvent source having a higher operating pressure than an operating pressure of the sample source, a separation column, a sample loop and an injector valve. The valve includes a stator and a rotor. The stator defines at least five fluidic ports in a seal surface of the stator in respective fluidic communication with the sample source, the solvent source, the separation column, a first end of the sample loop and a second end of the sample loop. The rotor has a seal surface that defines at least two grooves and contacts the seal surface of the stator. The rotor further defines at least two through-holes that extend from the seal surface of the rotor to a back surface of the rotor providing fluidic communication with a conduit disposed adjacent to the back surface of the rotor. The valve has a load state and an inject state. The load state disposes the sample loop in fluidic communication with the conduit, one of the at least two grooves, and the sample source. The inject state disposes the sample loop in fluidic communication with the solvent source and the separation column via the at least two grooves of the seal surface of the rotor.

Another embodiment of the invention features a method of performing chromatography. The method includes rotating a rotor to a load-state position that disposes a sample loop and a sample source in fluidic communication with a conduit disposed adjacent to a back surface of the rotor, loading a sample onto the sample loop from a sample source under a pressure less than a pressure of a solvent source, rotating the rotor to an inject-state position that disposes the solvent source in fluidic communication with a column via at least two grooves in a seal surface of the rotor and the sample loop, and injecting the loaded sample onto the column under the pressure of the solvent source.

BRIEF DESCRIPTION OF THE DRAWINGS

The drawings are not necessarily to scale, emphasis instead generally being placed upon illustrating some principles of the invention.

FIG. 2b is a bottom detailed view of a portion of the seal surface of the stator of FIG. 2a;

FIG. 3c is a detailed planar view of a central portion of the contact surface of the rotor of FIG. 3a;

FIG. 3e is a detailed planar view of a central portion of the back surface of the rotor of FIG. 3a;

FIGS. 4a, 4b and 4c are schematic views of a prior art valve, illustrating loading and injection of a sample.

DESCRIPTION

Multiport injector valves are well known to those of skill in the chromatography arts. For convenience, features of the invention are illustrated, herein, via descriptions of an embodiment of a modified six-port rotary shear injector valve. In view of the present description, one of skill will recognize that features of the invention are applicable to other types of injector valves, other valves used in chromatography and chemical processing, and, more generally, to other valves and mechanical devices that have components that experience shear surface forces due to sliding motions at component-contact surfaces.

Figure 1:
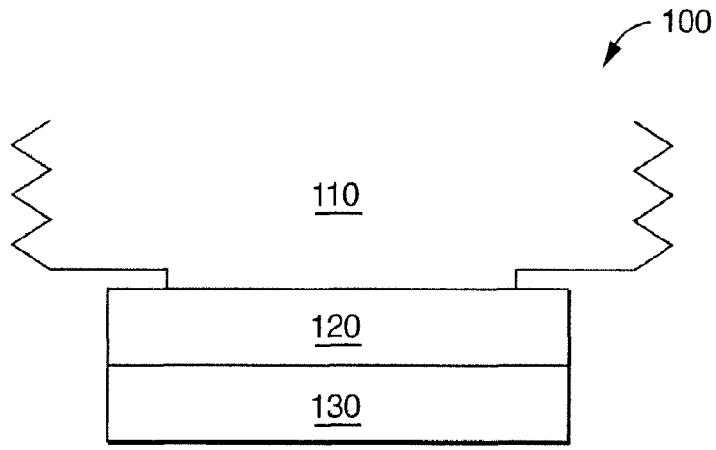
FIG. 1 is a block-diagram side view of a portion of an injector valve, in accordance with one embodiment of the invention.

FIG. 1 is a block diagram of a portion of an injector valve 100, suitable, for example, for HPLC or higher pressure LC, in accordance with one embodiment of the invention. The valve includes a stator 110, a rotor 120 and a back plate 130. The invention, in some aspects, relates to the disposition of conduits relative to front and back surfaces of the rotor. For simplicity, only the stator 110, rotor 120 and back plate 130 are illustrated and described.

Figure 2A:
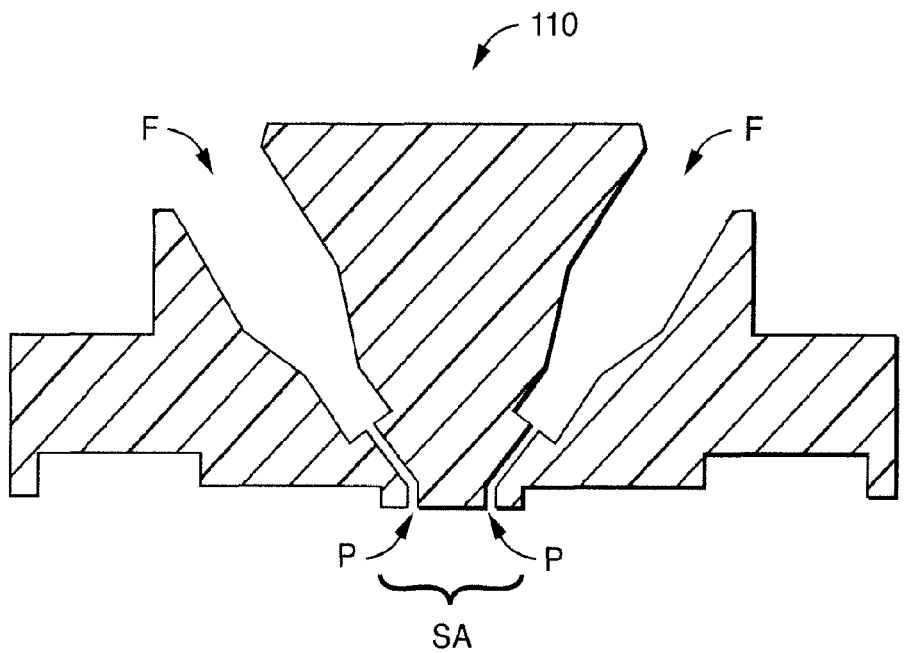
FIG. 2a is a cross-sectional side view of the stator of FIG. 1.

FIG. 2a is a cross-section side view of the stator 110. The stator has a seal/contact surface SA, which defines six ports that lead to six fittings F (two visible in the cross section). The fittings F permit tubing connections, as know in the HPLC art, to, for example, a solvent pump, a sample source, a sample loop, a waste line, and a separation column. The solvent pump preferably delivers solvent at pressures of at least approximately 1,000 psi, more preferably at least approximately 5,000 psi, still more preferably at least approximately 10,000 psi, or greater. The sample source is optionally based on a syringe pump, configured to deliver a sample at a pressure of, for example, approximately 500 psi.

Figure 2B:
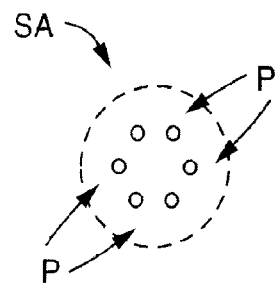

FIG. 2b is a planar detailed view of a portion of the seal surface SA of the stator 110. The seal surface SA has six ports P (openings), one for each of the six fittings F, as described above. As described in more detail below, the ports P in the seal surface SA of the stator 110 slidably mate with the rotor 120 to selectably provide fluidic pathways between pairs of the ports P, during operation of the valve 100.

Figure 3A:
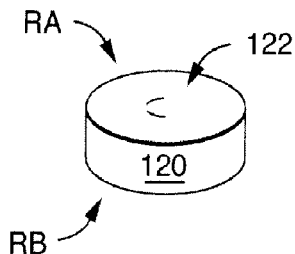
FIG. 3a is a three-dimensional view of the rotor of FIG. 1.
Figure 3B:
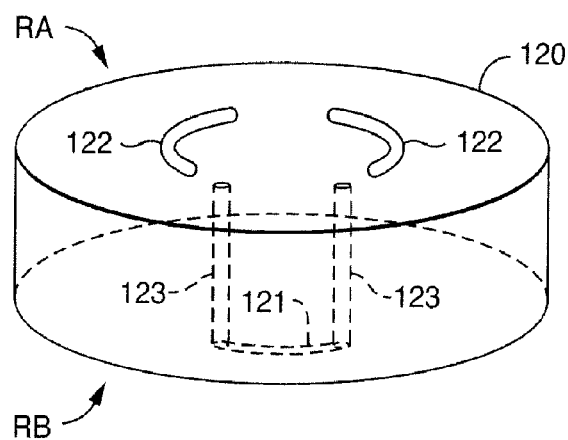
FIG. 3b is a three-dimensional see-through view of the rotor of FIG. 1.

FIG. 3a is a three-dimensional view of the rotor 120 and FIG. 3b is a three-dimensional see-through view of the rotor 120. The rotor 120 has a seal/contact surface RA that defines two grooves 122, which act as fluid conduits, in cooperation with the seal surface SA of the stator 110. The rotor 120 also has a back-surface groove 121, defined in the back surface RB of the rotor, and two through-holes 123 extending from the seal surface RA to the back surface RB to connect with the ends of the back-surface groove 121.

During use of the valve 100, the rotor 120 is rotated while generally being pressed in contact with the stator 110. The two grooves 122 of the seal surface RA and the groove 121 of the back surface RB (via the through-holes 123) mate with different pairs of ports P in the seal surface SA of the stator 110, depending on the state of the valve 100, to fluidically connect various components of an apparatus, i.e., in this example, a solvent pump, a sample source, a sample loop, a waste line, and a separation column.

Figure 3C:
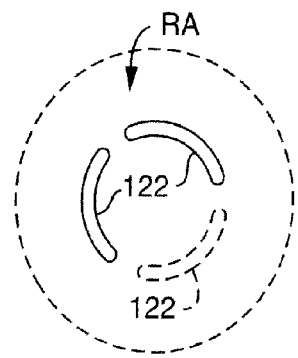

FIG. 3c is a detailed planar view of a central portion of the seal surface RA of the rotor 110, showing the two grooves 122. As noted, when the seal surfaces SA, RA of the stator 110 and rotor 120 are in contact, the grooves 122 help define fluidic conduits, to connect pairs of the ports P of the stator 110.

Figure 3D:
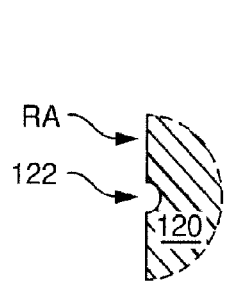
FIG. 3d is a cross-sectional detailed view of the rotor of FIG. 3a, showing a groove in the contact surface.

FIG. 3d is a cross-sectional detailed view of a central portion of the seal surface RA of the rotor 120, showing the cross-sectional configuration of one of the grooves 122 surface RA. The depth of the groove 122, in this example, is approximately 200 μm.

Figure 3E:
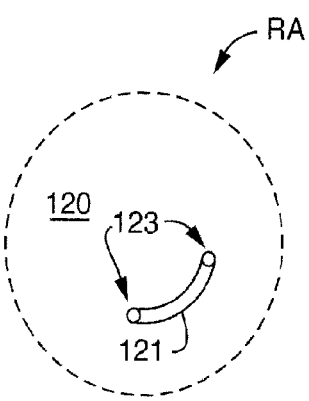

FIG. 3e is a detailed planar view of a central portion of a contact area of the back surface RB of the rotor 110, showing the groove 121 and end-on views of the two through-holes 123. By rotation of the rotor 120, against the stator 110, the pair of through-holes 123 is optionally aligned with a pair of the ports P. The through-holes 123 and a conduit—defined by the groove 121 in cooperation with a contact surface of the back plate 130—provide a fluidic pathway between the pair of the ports P.

In one alternative embodiment, a groove is defined in the contact surface of the back plate 130, as an alternative to, or in addition to, the groove 121 in the back surface RB of the rotor 110. In various embodiments, the back plate 130 is fixedly attached to the rotor 120 or is in slidable contact with the rotor.

Thus, in some embodiments, the rotor 120 and back plate 130 rotate relative to one another to support selection of fluidic pathways.

One alternative embodiment still uses three grooves, but all three grooves are disposed in the back surface RB of the rotor 120 or in the contact surface of the back plate 130. Such an embodiment potentially reduces wear associated with rotation of the rotor 120 relative to the stator 110, during a change in state of the valve 100. In view of the description provided herein, one of ordinary skill in the chromatography arts will recognize that various alternative embodiments include any number of grooves on a seal surface of a rotor, conduits disposed adjacent to the back surface of the rotor, and through-holes associated with the conduits adjacent to the back surface.

The stator 110 is formed of any suitable material(s), preferably a metal, which is optionally coated to improve, for example, friction and/or wear properties. Preferred metals include 316 stainless steel or titanium. The rotor 120 is preferably formed of a polymer, preferably reinforced. The rotor 120 is preferably formed of a material that is selected for its ability to form a liquid-tight seal at desired pressures.

Rotor and/or stator surfaces are optionally coated with, for example, a graphite, diamond or diamond-like coating (DLC). Optionally, a DLC coating has an added thin lubricating graphite layer, to assist, for example, break-in.

One suitable polymeric material is polyether-ether-ketone, such as PEEK polymer (available from Victrex PLC, Lancashire, United Kingdom.) Alternative polymers include, for example, fluoropolymers such as polytetrafluorothylene (available as TEFLON polymer from Dupont Engineering Polymers, Newark, Delware), chlorotetrafluoroethylene, polychlorotrifluoroethylene (available as NEOFLON PCTFE fluoropolymer from Fluorotherm Polymers, Inc., Fairfield, N.J.), and modified copolymer fluoropolymers (for example, a modified copolymer of tetrafluoroethylene and ethylene available as DUPONT TEFZEL fluoropolymer, which is resistant to concentrated nitric acid or sulfuric acid), and other polymers, such as polyimide (available as DUPONT VESPEL polyimide.)

In some embodiments, the rotor 120 is formed of a composite material. For example, in some of these embodiments, the rotor 120 is formed of a mixture of a polymer, such as polyether-ether-ketone, and about 5% by weight of glass, fiberglass, carbon, and/or or other particles and/or fibers.

The rotor 120 optionally includes a mixture of polymers, such as a combination of polyether-ether-ketone and tetrafluoroethelene. An optional combination of polyetheretherketone and tetrafluoroethelene has 50% to 90% polyetheretherketone and 10% to 50% tetrafluoroethelene, or 60% to 80% polyetheretherketone and 20% to 40% tetrafluoroethelene.

An example of a liquid chromatography apparatus, and a method of operating the apparatus, and their advantages relative to a prior art apparatus and method, are described next, with reference to FIGS. 4 and 5.

FIG. 4a is side block view of a prior art six-port injector valve 400. The valve 400 includes a stator 410 and a rotor 420. The stator is formed of stainless steel and the rotor is formed of polyether-ether-ketone. FIGS. 4b and 4c are planar-view diagrams of the interface between the rotor 420 and the stator 410 that illustrate operation of the prior art injector valve 400 in the context of an HPLC apparatus.

The stator 410 has six ports 1-6, which are connected to a solvent pump, a sample source, a sample loop 450, a waste line, and a separation column. The rotor 420 has three grooves in a seal surface that contacts the stator 410. The three grooves, in cooperation with the stator 410, define three conduits G1, G2, G3 (schematically illustrated by heavy lines.) Rotation of the rotor 420 between a load state (FIG. 4b) and an inject state (FIG. 4c) disposes the conduits G1, G2, G3 as desired respectively for loading of a sample onto the sample loop 450 and injecting of the loaded sample into a solvent stream flowing to the separation column.

When in the load state, two of the conduits G1, G3 fluidically connect the sample source to the waste line via the sample loop 450; the remaining conduit G2 connects the solvent source to the separation column. When in the inject state, two of the conduits G2, G3 connect the solvent source to the separation column, now via the sample loop 450, while the remaining conduit G1 connects the sample source directly to the waste line. Hence, in either state, one conduit G2 is only exposed to the pressure of the solvent source, one conduit G3 is exposed alternately to the pressure of the solvent source and the pressure of the sample source, and the remaining conduit G1 is only exposed to the pressure of the sample source.

In some common LC apparatus, the sample source operates at a much lower pressure than a solvent source. For example, a sample source can include a syringe pump that delivers a sample at a pressure of 500 psi, while the solvent source can include a solvent pump that delivers a solvent at a pressure of up to 4,000 to 5,000 psi in, for example, an HPLC apparatus, or up to 15,000 psi or greater in, for example, a UHPLC apparatus. Thus, one of the conduits, i.e., the conduit G1, in the present prior art example, only experiences relatively lower pressures relative to the pressure of a solvent pump.

To maintain a fluid-tight seal interface between the rotor 420 and the stator 410, a compressive force is applied to the rotor, to typically provide a greater pressure on the interface than the pressure of the solvent flowing through the conduits G2, G3. Since the rotor 420 is formed of polyether-etherketone, the grooves are susceptible to deformation and collapse, due to the compressive force, which can affect the reliability, performance and/or lifetime of the valve 400. The compressive stress is mitigated, however, for the two conduits G2, G3 that experience a balancing effect of the pressure applied by the solvent, at least during a portion of the time of operation of the valve 400. The third conduit G1, however, which never experiences the high pressure of the solvent, is particularly vulnerable to the effects of the compressive force.

Figures 5A, 5B, 5C:
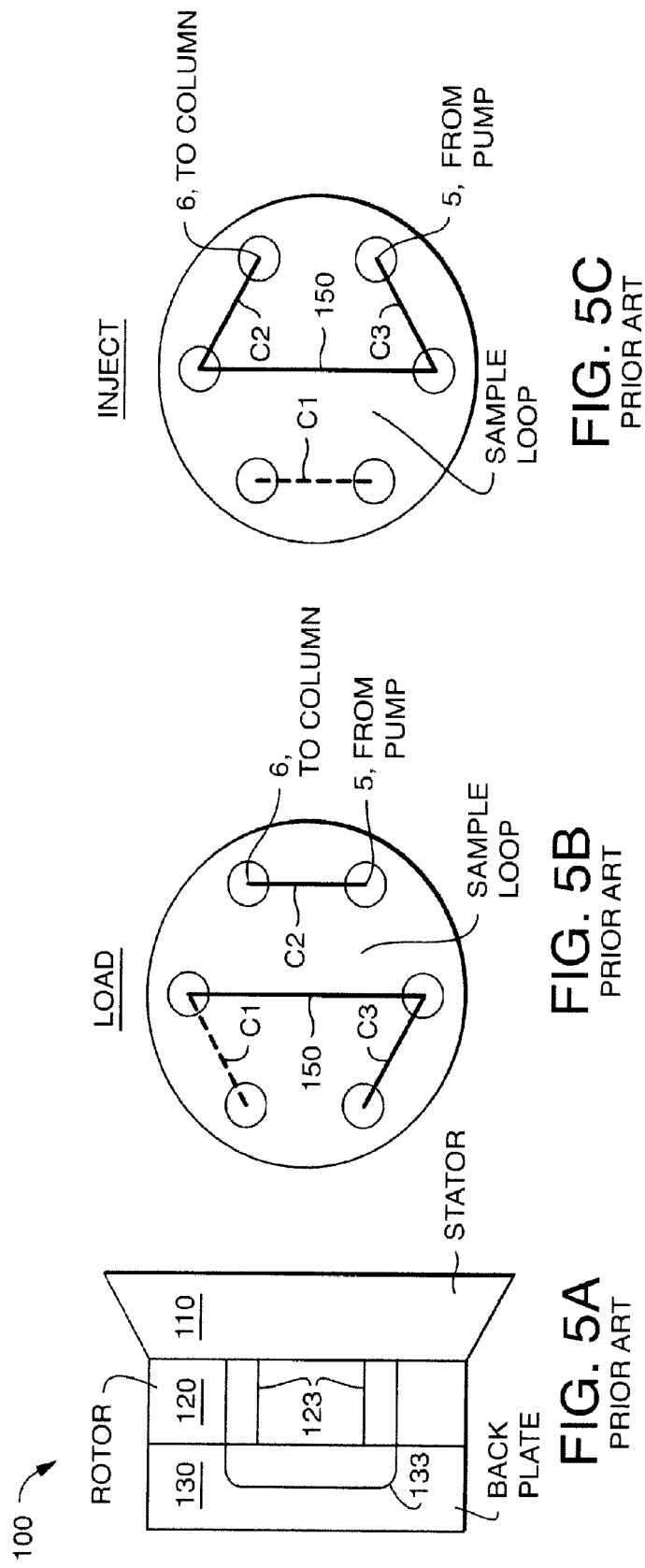
FIGS. 5a, 5b and 5c are schematic views of an injector valve, illustrating loading and injection of a sample, in accordance with an embodiment of the invention.

FIG. 5a is side block view of a particular implementation example of the valve 100 described above, in which the conduit adjacent to the back surface RB of the rotor 120 is implemented with a groove 133 in the surface of the back plate 130. As illustrated in FIG. 1, preferably, the contact area between the back plate 130 and the rotor 120 is greater than the contact area between the rotor 120 and the stator 110. Thus, for a particular force applied to the back plate 130, a greater compressive stress will exist at the interface between the rotor 120 and stator 110 than at the interface between the back plate 130 and rotor 120. In turn, the conduit, including the groove 133, adjacent to the back surface RB of the rotor 120 will experience less stress related to interfacial forces than will the two grooves 122 of the seal surface RA of the rotor 120; thus, where the back plate 130 and/or the rotor 120 are formed of deformable material, the material adjacent to the back surface RB of the rotor 120 will be less subject to deformation and collapse than material adjacent to the seal surface RA of the rotor 120.

Optionally, in other embodiments, a back plate, a rotor and/or a stator are shaped to accommodate different interfacial stresses. That is, for example, the sides of a rotor optionally taper from a larger back-plate-contacting surface to a smaller stator-contacting surface.

For illustrative purposes, the following details provide a specific example of one embodiment of the invention. In this example, the valve 100 is included in an UHPLC apparatus. The stator 110 is formed of stainless steel and the rotor 120 is formed of reinforced PEEK polymer. The stator 110 has six ports 1-6, which are connected to a solvent pump operating at a pressure of approximately 15,000 psi, a sample source operating at a pressure of approximately 500 psi, a sample loop, a waste line, and a separation column.

In this example, a load of approximately 500 lbs is applied to the back plate 130, providing a compressive stress of approximately 10,200 psi at the interface (area approximately 0.049 inch$^2$) between the back plate 130 and rotor 120 and a compressive stress of approximately 18,600 psi at the interface (area of approximately 0.027 inch$^2$) between the rotor 120 and stator 110. The stress at the interface between the rotor 120 and stator 110 is chosen, in part, to exceed the yield strength of the PEEK polymer, to assist formation of a liquid-tight interface. The stress at the interface between the back plate 130 and rotor 120 is less than the yield stress of the PEEK polymer.

FIGS. 5b and 5c are planar-view diagrams of the two interfaces between the stator 110, the rotor 120, and the back plate 130, which illustrate one example of operation of the valve 100. As for the prior art stator 410, the example stator 110 has six ports 1-6, which are connected to a solvent source, a sample source, a sample loop 150, a waste line, and a separation column. The two grooves 122 of the seal surface RA of the rotor 120 define two conduits C2, C3 (schematically illustrated by heavy lines) in cooperation with the seal surface SA of the stator 110, while the groove 133 of the back plate 130 defines a conduit C1 (schematically illustrated by a dashed line) in cooperation with the back surface RB of the rotor 120.

Rotation of the rotor 120- and the back plate 130, whose rotational orientation is fixed relative to the rotor 120—between a load state (FIG. 5b) and an inject state (FIG. 5c) disposes the conduits C1, C2, C3 as desired respectively for loading of a sample onto the sample loop 150 and injecting of the loaded sample into a solvent stream flowing to the separation column.

When in the load state, the conduits C1, C3—and the through-holes 123 in communication with the conduit C1—fluidically connect the sample source to the waste line via the sample loop 150; the remaining conduit C2 connects the solvent source to the separation column. When in the inject state, two of the conduits C2, C3 connect the solvent source to the separation column, now via the sample loop 150, while the remaining conduit C1 connects the sample source directly to the waste line. Hence, in the two states, one conduit C2 is only exposed to the pressure of the solvent source, one conduit C3 is exposed alternately to the pressure of the solvent source and the pressure of the sample source, and the remaining conduit C1 (which is located adjacent to the back surface RB of the rotor 120) is only exposed to the pressure of the sample source.

In this example, the valve 100 exploits the relatively low pressures experienced by the conduit C1 by disposing the conduit C1 adjacent to the back surface RB of the rotor 120 and subjecting the conduit C1 to a lower compressive stress than required for the conduits C2, C3 disposed in the seal surface RA of the rotor 120. The polymer material of the rotor 120, in the vicinity of the conduit C1, is thus less subject to damage, in comparison, for example, to the situation for the conduit G1 in the prior art device described above.

Variations, modifications, and other implementations of what is described herein will occur to those of ordinary skill in the art without departing from the scope of the invention as described. For example, in view of the above description, it will be apparent that the number and/or arrangement of various components of the above-described injector valve 100 are optionally modified, while still exploiting features of the invention. For example, alternative embodiments of the invention include other types of valves having sliding surfaces and applications in LC, such as vent valves, switching valves and diverter valves. Thus the terms "rotor" and "stator" refer, more generally, to components that slide against one another, in any of these embodiments. Accordingly, the invention is to be defined not by the preceding illustrative description but instead by the scope of the following claims.

What is claimed is:

1. A chromatography apparatus, comprising:
   a sample source;
   a solvent source having a higher operating pressure than an operating pressure of the sample source;
   a separation column;
   a sample loop; and
   an injector valve, comprising,
      a stator defining at least five fluidic ports in a seal surface of the stator in respective fluidic communication with the sample source, the solvent source, the separation column, a first end of the sample loop and a second end of the sample loop; and
      a rotor, having a seal surface that defines at least two grooves and contacts the seal surface of the stator, the rotor further defining at least two through-holes that extend from the seal surface of the rotor to a back surface of the rotor providing fluidic communication with either end of a conduit disposed adjacent to the back surface of the rotor,
      wherein the valve has a load state that disposes the sample loop in fluidic communication with the conduit adjacent to the back surface, one of the at least two grooves, and the sample source, and wherein the valve has an inject state that disposes the sample loop in fluidic communication with the solvent source and the separation column via the at least two grooves of the seal surface of the rotor.

2. The apparatus of claim 1, wherein the pressure of the solvent source is greater than 2,000 psi and the pressure of the sample source is less than 2,000 psi.

3. The apparatus of claim 2, wherein the pressure of the solvent source is greater than 10,000 psi and the pressure of the sample source is less than 1,000 psi.

4. A method of performing chromatography, comprising:
   providing an rotary injector valve comprising
      a stator defining at least five fluidic ports in a seal surface of the stator in respective fluidic communication with a sample source, a solvent source, a separation column, a first end of a sample loop and a second end of a sample loop, and
      a rotor having a seal surface defining at least two grooves and contacting the seal surface of the stator, the rotor defining at least two through-holes that extend from the seal surface of the rotor to a back surface of the rotor providing fluidic communication with either end of a conduit disposed adjacent to the back surface of the rotor;
   rotating the rotor to a load-state position that disposes the sample loop and the sample source in fluidic communication with the conduit;
   loading a sample onto the sample loop from the sample source under a pressure less than a pressure of the solvent source;
   rotating the rotor to an inject-state position that disposes the solvent source in fluidic communication with the column via the at least two grooves and the sample loop; and
   injecting the loaded sample onto the column under the pressure of the solvent source.

5. The method of claim 4, wherein the pressure of the solvent source is greater than about 5,000 psi and the pressure of the sample source is less than about 1,000 psi.

* * * * *